United States Patent [19]

Tuneki et al.

[11] Patent Number: 5,231,189
[45] Date of Patent: Jul. 27, 1993

[54] PROCESS FOR PRODUCING N-SUBSTITUTED AZIRIDINE COMPOUND

[75] Inventors: Hideaki Tuneki, Tokyo; Hitoshi Yano, Suita; Yuuji Shimasaki, Suita; Kimio Ariyoshi, Suita; Hideki Masada, Yokohama; Michio Ueshima, Takarazuka, all of Japan

[73] Assignee: Nippon Shokubai Co., Ltd., Osaka, Japan

[21] Appl. No.: 834,328

[22] PCT Filed: Jun. 21, 1991

[86] PCT No.: PCT/JP91/00835
§ 371 Date: Feb. 20, 1992
§ 102(e) Date: Feb. 20, 1992

[87] PCT Pub. No.: WO91/19696
PCT Pub. Date: Dec. 26, 1991

[30] Foreign Application Priority Data

Jun. 21, 1990 [JP] Japan .................................. 2-161236

[51] Int. Cl.$^5$ ............................................ C07D 203/06
[52] U.S. Cl. ..................................... 548/967; 548/968
[58] Field of Search ........................ 548/969, 967, 968

[56] References Cited

U.S. PATENT DOCUMENTS 3,502,654  3/1970  Young ............................. 260/239
4,841,060  6/1989  Hino et al. ....................... 548/969

FOREIGN PATENT DOCUMENTS 5010593  4/1975  Japan .................................. 548/969
9100835  6/1991  Japan .................................. 548/969

WO9119696  12/1991  Japan .................................. 548/969

*Primary Examiner*—Mary C. Lee
*Assistant Examiner*—Joseph K. McKane
*Attorney, Agent, or Firm*—Sherman and Shalloway

[57] ABSTRACT

The present invention provides a novel process for producing an N-substituted aziridine compound by subjecting an N-substituted alkanolamine to a gas-phase catalytic dehydration reaction (the following reaction formula).

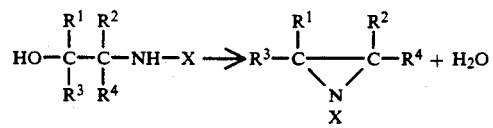

In the above formula, $R^1$, $R^2$, $R^3$ and $R^4$ are each independently one member of selected from a hydrogen atom and alkyl groups of 1–4 carbon atoms, and X is one member selected from alkyl groups of 1–4 carbon atoms, a cyclohexyl group, a phenyl group, a benzyl group, hydroxyalkyl groups of 1–4 carbon atoms and aminoalkyl groups of 1–4 carbon atoms.

Preferably, the N-substituted aziridine compound is produced at a high yield by subjecting an N-substituted alkanolamine to a gas-phase catalytic dehydration reaction in the presence of a silicon-containing or phosphorus-containing catalyst under the conditions of reaction pressure = 5–250 mmHg, reaction temperature = 300°–450° C. and space velocity = 50–500 hr$^{-1}$ (STP).

3 Claims, No Drawings

PROCESS FOR PRODUCING N-SUBSTITUTED AZIRIDINE COMPOUND

DETAILED DESCRIPTION OF THE INVENTION

1. Technical Field

The present invention relates to a novel process for producing an N-substituted aziridine compound by a gas-phase intramolecular dehydration reaction of an N-substituted alkanolamine in the presence of a catalyst. Since N-substituted aziridine compounds are cyclic amines each having a heterocyclic three-membered ring of large distortion and have both ring-opening reactivity and reactivity as an amine, they are very useful as various intermediates or as a raw material for amine type polymers or crosslinking agents.

2. Background Art

The following processes are known for production of N-substituted aziridine compounds. These conventional techniques, however, have the problems as mentioned below.

(a) A process which comprises converting an N-substituted ethanolamine to its ester with sulfuric acid and treating the ester with a concentrated alkali to give rise to ring closure to produce an N-substituted aziridine (U.S. Pat. No. 1,177,297). Using large amounts of auxiliary raw materials, the process gives a low productivity and produces, as by-products derived from the auxiliary raw materials, large amounts of inorganic salts of low utility value.

(b) A process which comprises conducting an intramolecular dehydration reaction of an N-substituted ethanolamine with diethoxytriphenylphospholan to convert said amine to an N-substituted aziridine compound [Journal of Organic Chemistry 51, (1986), 95-97]. The process cannot be employed as a practical process, because diethoxytriphenylphospholan is very expensive and moreover its recovery and reuse is impossible.

(c) A process which comprises subjecting aziridine to an addition reaction with an epoxy group-containing compound such as ethylene oxide to produce an N-substituted aziridine (U.S. Pat. No. 3,166,590). In the process, the epoxy compound adds successively to the produced N-substituted aziridine, causing an addition reaction. Hence, it is necessary to use aziridine in a considerable excess; even after such a measure, there are unavoidably formed by-products to which 2 to 3 moles of the epoxy compound have been added, lowering the yield of desired product. In the process, it is also necessary ordinarily to add an alkali in order to prevent aziridine from being polymerized; however, the addition of the alkali causes the polymerization of the epoxy compound, which is a contradiction. Hence, the production operation is carried out while a point of compromise is found out between the safety aspect and the polymerization control aspect.

(d) A process which comprises dimerizing ethyleneimine with an alkali metal catalyst to produce 1-(2-aminoethyl)aziridine (U.S. Pat. No. 3,502,654). In the process, the catalyst is a very dangerous alkali metal and, moreover, aziridine dimers and higher polymers are formed as by-products making the yield of desired product relatively low.

When it is intended to produce, in particular, an N-substituted aziridine compound whose substituent has a functional group such as hydroxyl group, amino group, acyl group or the like, any of the above processes makes the reaction complex and produces various by-products.

Thus, any of the above processes is not at all satisfactory viewed from the standpoint of industrial production.

The object of the present invention is to solve the above-mentioned problems and provide a novel process for producing an N-substituted aziridine compound from an N-substituted alkanolamine at a high selectivity at a high efficiency without using any auxiliary raw material.

DISCLOSURE OF THE INVENTION

The present inventors made study on a novel process for production of N-substituted aziridine compound. As a result, the present inventors found that an N-substituted aziridine compound can be produced at a high selectivity by subjecting an N-substituted alkanolamine to an intramolecular dehydration reaction in a gas phase in the presence of a catalyst. The finding has led to the completion of the present invention. The present invention resides in a process for producing an N-substituted aziridine compound represented by general formula (II)

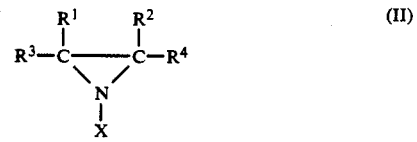

wherein $R^1$, $R^2$, $R^3$ and $R^4$ are each independently one member selected from a hydrogen atom and alkyl groups of 1-4 carbon atoms, and X is one member selected from alkyl groups 1-4 carbon atoms, a cyclohexyl group, a phenyl group, a benzyl group, hydroxyalkyl groups of 1-4 carbon atoms and aminoalkyl groups of 1-4 carbon atoms, the gist of which process comprises subjecting to a gas-phase intramolecular dehydration reaction in the presence of a catalyst an N-substituted alkanolamine represented by general formula (I)

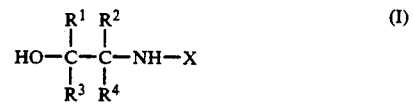

wherein $R^1$, $R^2$, $R^3$, $R^4$ and X each have the same definition as in general formula (II). According to the present invention, even when the substituent X has a reactive functional group, i.e. an amino group or a hydroxyl group, an N-substituted aziridine compound can be produced at a high selectivity with side reactions being suppressed and without giving rise to any change in the substituent. Further, since no auxiliary raw material is required, the present process is very advantageous also in economy. The present invention is hereinafter described in detail.

The present inventors made study on a process for production of N-substituted aziridine compound. As a result, the present inventors found that an N-substituted aziridine compound can be produced by subjecting an N-substituted alkanolamine to a gas-phase intramolecular dehydration reaction in the presence of a catalyst.

The finding has led to the completion of the present invention.

Specific examples of the N-substituted alkanolamine represented by the general formula (I) used as a raw material in the present invention, are N-substituted alkanolamines whose amino group has an alkyl group as a substituent, such as N-methylethanolamine, N-ethylethanolamine, N-butylethanolamine and the like; and N-substituted alkanolamines whose amino group has a functional group as a substituent, such as diethanolamine, N-(2-aminoethyl)ethanolamine, N-acetylethanolamine and the like. These N-substituted alkanolamines can be converted to corresponding N-substituted aziridine compounds represented by the general formula (II), according to the process of the present invention.

The catalyst used in the present invention is preferably a phosphorous-containing catalyst or a silicon-containing catalyst.

Recommendable as the phosphorous-containing catalyst is a composition represented by the general formula $X_aP_bM_cO_d$ wherein X represents at least one element selected from the elements of group IIIA of periodic table, the elements of group IVA, the elements of group VA, the transition metal elements of groups I and VIII, the lanthanide elements and the actinide elements, P represents phosphorus, M represents at least one element selected from the alkali metal elements and the alkaline earth metal elements, O represents oxygen, the suffixes a, b, c and d represent the ratios of the atom numbers of the individual elements, when a is 1, b=0.01 to 6 (preferably 0.1 to 3) and c=0.01 to 3 (preferably 0.05 to 2), and d is a value determined by the values of a, b and c and further by the state of bonding of the constituent elements.

Recommendable as the silicon-containing catalyst is a composition represented by the general formula $Si_aM_bY_cO_d$ wherein Si represents silicon, M represents at least one element selected from the alkali metal elements and the alkaline earth metal elements, Y represents at least one element selected from boron, aluminum, titanium, zirconium, tin, zinc and cerium, O represents oxygen, the suffixes a, b, c and d represent the ratio of the atom numbers of the individual elements, when a is 1, b=0.005 to 1 (preferably 0.01 to 0.6) and c=0.005 to 1 (preferably 0.005 to 0.2), and d is a value determined by the values of a, b and c and further by the state of bonding of the constituent elements.

In practicing the present invention, the reactor can be any of a fixed bed type and a fluidized bed type, but a fixed bed type is preferable. The reaction pressure can be any of normal pressure, elevated pressure and reduced pressure. It is possible to dilute the raw material N-substituted ethanolamine with an inert gas such as nitrogen, argon or the like, as necessary. It is also possible to feed, optionally, ammonia, water or the like together with the N-substituted ethanolamine in order to suppress side-reactions.

The preferable reaction conditions when dilution with inert gas is conducted, are generally such that the concentration of N-substituted ethanolamine is 1–30% by volume, the reaction temperature is in the range of 300°–500° C., more preferably 350°–450° C., and the space velocity of raw material gas is in the range of 10–10000 hr$^{-1}$ (STP), more preferably 50–5000 hr$^{-1}$ (STP). Too high a concentration of N-substituted ethanolamine invites reduction in yield, and too low a concentration gives poor productivity. If the reaction temperature is too high, a carbon-like deposit is rapidly accumulated on the catalyst shortening the catalyst life; side reactions take place more vigorously reducing the yield; disadvantages are incurred also in equipment and utility. Meanwhile, if the reaction temperature is too low, the activity is insufficient reducing the yield. If the space velocity is too low, a larger reactor is required and a lower productivity is obtained. If the space velocity is too high, the gas flow rate is too large increasing the pressure loss in the catalyst layer and the reaction does not proceed smoothly reducing the conversion and consequently the yield. The catalyst layer is preferably not too long because a long catalyst layer makes the pressure loss large and consequently makes the inlet pressure high when the space velocity is high.

When an inert gas or the like is used, however, the produced N-substituted aziridine compound accompanies the inert gas and thereby may be lost without being captured. Further, since the inert gas is used in a large amount, the cost is large and, when the inert gas is recovered and recirculated for reuse, the process steps are complex making the facility cost high. In this respect, a process is preferable in which a reaction is conducted at a 100% concentration of N-substituted alkanolamine using substantially no inert gas or the like. In this case, the preferable reaction conditions are generally such that the reaction pressure is in the range of 5–250 mmHg (absolute pressure), the reaction temperature is in the range of 300°–450° C. and the space velocity is in the range of 50–500 hr$^{-1}$ (STP). If the reaction temperature is too low, it is difficult to capture the reaction product sufficiently, and the vacuum equipment has a high load incurring a disadvantage in facility. The same description as given above, also applies to the reaction temperature and the space velocity.

More optimum reaction conditions differ by the type or raw material, i.e. N-substituted alkanolamine. They differ also by the production policy, for example, a policy wherein a high selectivity is aimed at even by slightly reducing the conversion of N-substituted alkanolamine and unreacted raw material is recovered and reused, or a policy wherein a higher per-pass yield is aimed at without recovering unreacted raw material. The latter policy is generally adopted because the production of N-substituted aziridine intended by the present invention is made on a small scale. Next are described the preferable reaction conditions for production of N-substituted aziridine compound at a higher yield when various types of N-substituted alkanolamines represented by the general formula (I) are used.

When the X of the formula (I) is an alkyl group of 1–4 carbon atoms, a cyclohexyl group, a phenyl group or a benzyl group, it is preferable that the gas-phase intramolecular dehydration reaction be conducted at a reaction pressure in the range of 10–250 mmHg (absolute pressure) at a reaction temperature in the range of 300°–450° C. at a space velocity in the range of 50–500 hr$^{-1}$ (STP).

When the X of the formula (I) is a hydroxyalkyl group of 1–4 carbon atoms, or an aminoalkyl group of 1–4 carbon atoms, such an N-substituted alkanolamine has at least 3 functional groups in total each of high reactivity, making the reaction complex. In the case of, for example, N-(2-aminoethyl)ethanolamine, piperazine is produced as a by-product in addition to desired 1-(2-amino-dethyl)aziridine, and the by-product piperazine is produced in a large amount unless the catalyst composition and the reaction conditions are selected appropriately. Also in the case of, for example, diethanolamine, the formation of morpholine owing to the intramolecular dehydration reaction between OH groups is unlikely; however, owing to the high reactivity of the raw material, various side reactions including intermolecular reactions take place easily reducing the selectivity of 1-(2-hydroxyethyl)aziridine. Further, since the raw material has a high boiling point and the reaction product contains many kinds of by-products having boiling points close to the boiling point of unreacted raw material, the recovery of unreacted raw material is very difficult. Hence, in producing these N-substituted aziridine compounds, it is particularly advantageous to increase the conversion of N-substituted alkanolamine to achieve a higher per-pass yield. To realize it, the gas-phase intramolecular dehydration reaction is preferably conducted under the conditions of a reaction pressure in the range of 5-50 mmHg (absolute pressure), a reaction temperature in the range of 300°-450° C. and a space velocity in the range of 50-500 hr$^{-1}$ (STP).

INDUSTRIAL APPLICABILITY

The process of the present invention enables production of N-substituted aziridine compound from N-substituted alkanolamine at a high selectivity.

The process of the present invention is a novel process and can produce an N-substituted aziridine compound of high utility value at a very high efficiency. The process also has high superiority for industrial application.

BEST MODE FOR CARRYING OUT THE INVENTION

The present invention is hereinafter described in detail by way of Examples. In the present invention, the conversion of N-substituted alkanolamine and the selectivity and yield of N-substituted aziridine compound have the following definitions.

---
Conversion of N-substituted alkanolamine =
[N-substituted alkanolamine (moles) consumed
in reaction]/[N-substituted alkanolamine
(moles) fed into reactor] × 100
Selectivity of N-substituted aziridine compound =
[N-substituted aziridine compound (moles)
produced]/[N-substituted alkanolamine
(moles) consumed in reactor] × 100
Yield of N-substituted aziridine compound =
[N-substituted aziridine compound (moles)
produced]/[N-substituted alkanolamine
(moles) fed into reactor] × 100
---

Catalyst Preparation (1) Preparation of a catalyst having a composition of $Al_{0.9}Cd_{0.1}P_{0.9}$ In 500 ml of water were dissolved 168.8 g of aluminum nitrate nonahydrate and 11.8 g of cadmium nitrate. Thereto was added 51.9 g of 85 wt. % phosphoric acid with stirring. The resulting mixture was concentrated with heating and the concentrate was dried at 120° C. for 12 hours. The resulting solid was ground into 5-9 meshes and calcined at 1000° C. to obtain a catalyst having a composition of $Al_{0.9}Cd_{0.1}P_{0.9}$ in terms of atomic ratios excluding oxygen.

(2) Preparation of a catalyst having a composition of $Si_1Cs_{0.1}Ca_{0.05}B_{0.1}$ In 500 ml of water were dissolved 16.3 g of cesium carbonate and 3.7 g of calcium hydroxide with heating. Then 6.2 g of boric acid and 60 g of silica gel were added. The resulting mixture was concentrated with heating and stirring. The concentrate was dried at 120° C. for 15 hours. The resulting solid was ground into 5-9 meshes and calcined at 700° C. to obtain a catalyst having a composition of $Si_1Cs_{0.1}Ca_{0.05}B_{0.1}$ in terms of atomic ratios excluding oxygen.

(3) Preparation of a catalyst having a composition of $Cs_{0.9}K_{0.1}P_{0.8}Al_{0.01}$ In 300 g of water were dissolved 17.5 g of cesium nitrate, 0.56 g of potassium hydroxide and 9.2 g of 85 wt. % phosphoric acid. Thereto were added 60 g of silica gel as a carrier and 0.38 g of aluminum nitrate in this order. The resulting mixture was concentrated with heating and the concentrate was dried to 120° C. for 12 hours. The resulting solid was ground into 5-9 meshes and calcined at 700° C. for 4 hours to obtain a catalyst having a composition of $Cs_{0.9}K_{0.1}P_{0.8}Al_{0.01}$ in terms of atomic ratios excluding silicon of carrier silica gel and oxygen.

(4) Preparation of a catalyst having a composition of $Si_1Ba_{0.1}Al_{0.1}$

In 500 ml of water were dissolved 31.5 g of barium hydroxide octahydrate and 37.5 g of aluminum nitrate nonahydrate with heating. Then, 60 g of silica gel was added. The resulting mixture was concentrated with heating and stirring. The concentrate was dried at 120° C. for 12 hours. The resulting solid was ground into 5-9 meshes and calcined at 600° C. to obtain a catalyst having a composition of $Si_1Ba_{0.1}Al_{0.1}$ in terms of atomic ratios excluding oxygen.

(5) Preparation of a catalyst having a composition of $Mg_1P_{0.5}Na_{0.1}$

In 200 ml of water were suspended 58.1 g of magnesium hydroxide and 4.0 g of sodium hydroxide. Thereto was added 57.6 g of 85 wt. % phosphoric acid. The resulting mixture was concentrated with heating and sufficient stirring. The concentrate was evaporated to dryness on a hot water bath. The residue was dried at 120° C. for 12 hours in the air, then ground into 5-9 meshes, and calcined at 700° C. for 5 hours to obtain a catalyst having a composition of $Mg_1P_{0.5}Na_{0.1}$ in terms of atomic ratios excluding oxygen.

(6) Preparation of a catalyst having a composition of $Si_1Ba_{0.1}A_{0.1}$

In 500 ml of water were dissolved 31.5 g of barium hydroxide octahydrate and 37.5 g of aluminum nitrate nonahydrate with heating. Then, 60 g of silica gel was added. The resulting mixture was concentrated with heating and stirring. The concentrate was dried at 120° C. for 12 hours. The resulting solid was ground into 5-9 meshes and calcined at 600° C. to obtain a catalyst having a composition of $Si_1Ba_{0.1}Al_{0.1}$ in terms of atomic ratios excluding oxygen.

(7) Preparation of a catalyst having a composition of $Cs_{0.9}Ba_{0.1}P_{0.8}$

In 300 g of water were dissolved 17.5 g of cesium nitrate, 3.2 g of barium hydroxide and 9.2 g of 85 wt. % phosphoric acid. Thereto was added 60 g of a silica gel powder as a carrier. The resulting mixture was concentrated with heating. The concentrate was dried at 200° C. for 12 hours in the air. The resulting solid was ground into 5-9 meshes and calcined at 700° C. for 4 hours to obtain a catalyst having a composition of $Cs_{0.9}Ba_{0.1}P_{0.8}$ in terms of atomic ratios excluding silicon of carrier silica gel and oxygen.

Reaction

Example 1

20 ml of the catalyst having a composition of $Al_{0.9}Cd_{0.1}P_{0.9}$, prepared in accordance with the catalyst preparation (1) was filled into a stainless steel reaction tube of 16 mm in inside diameter. The reaction tube was then immersed in a molten salt bath of 400° C., and a raw material gas of N-methylethanolamine:nitrogen=5:95 in terms of volume ratio was passed through the reaction tube at a space velocity of 4000 $hr^{-1}$ (STP) to give rise to a reaction. The reaction product after 2 hours from the start of the reaction was analyzed by gas chromatography to obtain the results shown in Table 1.

Example 2-21

Reactions and analyses were conducted in the same manner as in Example 1 except that there were employed the catalyst composition, type of raw material (N-substituted alkanolamine), concentration and space velocity of raw material gas, and reaction temperature as shown in Table 1. The results shown in Table 1 were obtained.

Example 22-37

Reactions and analyses were conducted in the same manner as in Example 1 except that there were employed the catalyst composition, type of raw material (N-substituted alkanolamine), concentration and space velocity of raw material gas, and reaction temperature as shown in Table 2. The results shown in Table 2 were obtained.

TABLE 1

| Example | Catalyst composition | N-substituted alkanolamine (I) as raw material | N-substituted aziridine compound (II) as product | Reaction pressure (mmHg) |
|---|---|---|---|---|
| 1 | $Al_{0.9}Cd_{0.1}P_{0.9}$ | N-methylethanolamine | N-methylaziridine | Normal pressure |
| 2 | $Al_{0.9}Cd_{0.1}P_{0.9}$ | N-methylethanolamine | N-methylaziridine | Normal pressure |
| 3 | $Si_1Cs_{0.1}Ca_{0.05}Ba_{0.1}$ | N-methylethanolamine | N-methylaziridine | Normal pressure |
| 4 | $Cs_{0.9}K_{0.1}P_{0.8}Al_{0.01}$ | N-methylethanolamine | N-methylaziridine | 80 |
| 5 | $Cs_{0.9}K_{0.1}P_{0.8}Al_{0.01}$ | N-methylethanolamine | N-methylaziridine | 300 |
| 6 | $Al_{0.9}Cd_{0.1}P_{0.9}$ | N-ethylethanolamine | N-ethylaziridine | Normal pressure |
| 7 | $Al_{0.9}Cd_{0.1}P_{0.9}$ | N-ethylethanolamine | N-ethylaziridine | Normal pressure |
| 8 | $Cs_{0.9}K_{0.1}P_{0.8}Al_{0.01}$ | N-ethylethanolamine | N-ethylaziridine | 10 |
| 9 | $Al_{0.9}Cd_{0.1}P_{0.9}$ | N-propylethanolamine | N-propylaziridine | Normal pressure |
| 10 | $Cs_{0.9}K_{0.1}P_{0.8}Al_{0.01}$ | N-propylethanolamine | N-propylaziridine | 250 |
| 11 | $Cs_{0.9}K_{0.1}P_{0.8}Al_{0.01}$ | N-isopropyl-ethanolamine | N-isopropyl-aziridine | Normal pressure |
| 12 | $Cs_{0.9}K_{0.1}P_{0.8}Al_{0.01}$ | N-(n-butyl)-ethanolamine | N-(n-butyl)-aziridine | Normal pressure |
| 13 | $Cs_{0.9}K_{0.1}P_{0.8}Al_{0.01}$ | N-(n-butyl)-ethanolamine | N-(n-butyl)-aziridine | Normal pressure |
| 14 | $Cs_{0.9}K_{0.1}P_{0.8}Al_{0.01}$ | N-(t-butyl)-ethanolamine | N-(t-butyl)-aziridine | Normal pressure |
| 15 | $Si_1Ba_{0.1}Al_{0.1}$ | N-cyclohexyl-ethanolamine | N-cyclohexyl-aziridine | Normal pressure |
| 16 | $Mg_1Na_{0.1}P_{0.5}$ | N-phenylethanolamine | N-phenylaziridine | Normal pressure |
| 17 | $Si_1Ba_{0.1}Al_{0.1}$ | N-phenylethanolamine | N-phenylaziridine | 80 |
| 18 | $Si_1Ba_{0.1}Al_{0.1}$ | N-benzylethanolamine | N-benzylaziridine | Normal pressure |
| 19 | $Si_1Ba_{0.1}Al_{0.1}$ | N-benzylethanolamine | N-benzylaziridine | Normal pressure |
| 20 | $Cs_{0.9}K_{0.1}P_{0.8}Al_{0.01}$ | N-methyl-isopropanolamine | N-methyl-2-methylaziridine | Normal pressure |
| 21 | $Cs_{0.9}K_{0.1}P_{0.8}Al_{0.01}$ | N-methylamine-1-butanol | N-methyl-2-ethylaziridine | Normal pressure |

| Example | Space velocity ($hr^{-1}$) | Reaction temperature (°C.) | Raw material concentration (vol, %) | Elapsed time of reaction (hr) | Conversion of (I) (mole %) | Selectivity of (II) (mole %) | Per-pass yield of (II) (mole %) |
|---|---|---|---|---|---|---|---|
| 1 | 4000 | 400 | 5 | 2 | 50.3 | 65.2 | 32.8 |
| 2 | 40 | 380 | 5 | 2 | 87.5 | 23.6 | 20.7 |
| 3 | 1500 | 400 | 5 | 2 | 44.4 | 86.7 | 38.5 |
| 4 | 100 | 400 | 100 | 2 | 64.2 | 81.6 | 52.4 |
| 5 | 100 | 400 | 100 | 2 | 72.9 | 40.0 | 29.2 |
| 6 | 4000 | 430 | 30 | 2 | 46.0 | 66.6 | 30.6 |
| 7 | 4000 | 430 | 40 | 2 | 40.1 | 42.1 | 16.9 |
| 8 | 50 | 350 | 100 | 2 | 50.0 | 84.3 | 42.2 |
| 9 | 1000 | 350 | 1 | 2 | 43.9 | 76.7 | 33.7 |
| 10 | 500 | 450 | 100 | 2 | 41.6 | 80.1 | 33.3 |
| 11 | 5000 | 430 | 10 | 2 | 46.2 | 80.0 | 37.0 |
| 12 | 4000 | 420 | 5 | 2 | 56.9 | 90.8 | 51.7 |
| 13 | 10,000 | 450 | 5 | 2 | 60.1 | 88.4 | 53.1 |
| 14 | 2500 | 400 | 20 | 2 | 57.3 | 82.6 | 47.3 |
| 15 | 2000 | 400 | 5 | 2 | 59.6 | 73.9 | 44.0 |
| 16 | 4000 | 400 | 5 | 2 | 51.5 | 67.1 | 34.6 |
| 17 | 200 | 380 | 100 | 2 | 54.8 | 82.1 | 45.0 |
| 18 | 3000 | 420 | 5 | 2 | 49.1 | 78.2 | 38.4 |
| 19 | 3000 | 480 | 5 | 2 | 79.6 | 31.0 | 24.7 |
| 20 | 3000 | 410 | 5 | 2 | 59.8 | 82.6 | 49.4 |
| 21 | 2000 | 390 | 5 | 2 | 55.5 | 83.3 | 46.2 |

TABLE 2

| | N-substituted | N-substituted | Reaction |

TABLE 2-continued

| Example | Catalyst composition | alkanolamine (I) as raw material | aziridine compound (II) as product | pressure (mmHg) |
|---|---|---|---|---|
| 22 | $Al_{0.9}Cd_{0.1}P_{0.9}$ | N-aminoethyl-ethanolamine | N-aminoethyl-aziridine | Normal pressure |
| 23 | $Al_{0.9}Cd_{0.1}P_{0.9}$ | N-aminoethyl-ethanolamine | N-aminoethyl-aziridine | Normal pressure |
| 24 | $Cs_{0.9}K_{0.1}P_{0.8}Al_{0.01}$ | N-aminoethyl-ethanolamine | N-aminoethyl-aziridine | Normal pressure |
| 25 | $Mg_1Na_{0.1}P_{0.5}$ | N-aminoethyl-ethanolamine | N-aminoethyl-aziridine | Normal pressure |
| 26 | $Si_1Ba_{0.1}Al_{0.1}$ | N-aminoethyl-ethanolamine | N-aminoethyl-aziridine | Normal pressure |
| 27 | $Si_1Cs_{0.1}Ca_{0.05}Ba_{0.1}$ | N-aminoethyl-ethanolamine | N-aminoethyl-aziridine | Normal pressure |
| 28 | $Si_1Cs_{0.1}Ca_{0.05}Ba_{0.1}$ | N-aminoethyl-ethanolamine | N-aminoethyl-aziridine | Normal pressure |
| 29 | $Cs_{0.9}Ba_{0.1}P_{0.8}$ | N-aminoethyl-ethanolamine | N-aminoethyl-aziridine | 20 |
| 30 | $Cs_{0.9}K_{0.1}P_{0.8}Al_{0.01}$ | Diethanolamine | N-hydroxy-ethylaziridine | Normal pressure |
| 31 | $Si_1Ba_{0.1}Al_{0.1}$ | Diethanolamine | N-hydroxy-ethylaziridine | Normal pressure |
| 32 | $Si_1Ba_{0.1}Al_{0.1}$ | Diethanolamine | N-hydroxy-ethylaziridine | 20 |
| 33 | $Cs_{0.9}Ba_{0.1}P_{0.8}$ | Diethanolamine | N-hydroxy-ethylaziridine | 10 |
| 34 | $Cs_{0.9}Ba_{0.1}P_{0.8}$ | Diethanolamine | N-hydroxy-ethylaziridine | 20 |
| 35 | $Cs_{0.9}Ba_{0.1}P_{0.8}$ | Diethanolamine | N-hydroxy-ethylaziridine | 40 |
| 36 | $Cs_{0.9}Ba_{0.1}P_{0.8}$ | Diethanolamine | N-hydroxy-ethylaziridine | 150 |
| 37 | $Cs_{0.9}Ba_{0.1}P_{0.8}$ | Diethanolamine | N-hydroxy-ethylaziridine | 20 |

| Example | Space velocity ($hr^{-1}$) | Reaction temperature (°C.) | Raw material concentration (vol. %) | Elapsed time of reaction (hr) | Conversion of (I) (mole %) | Selectivity of (II) (mole %) | Per-pass yield of (II) (mole %) |
|---|---|---|---|---|---|---|---|
| 22 | 4000 | 400 | 5 | 2 | 50.3 | 65.2 | 32.8 |
| 23 | 1500 | 400 | 30 | 2 | 36.0 | 60.8 | 21.9 |
| 24 | 4000 | 400 | 5 | 2 | 78.1 | 72.9 | 56.9 |
| 25 | 4000 | 400 | 5 | 2 | 76.8 | 74.1 | 56.9 |
| 26 | 2000 | 400 | 5 | 2 | 51.6 | 61.1 | 31.5 |
| 27 | 1500 | 400 | 5 | 2 | 50.0 | 60.9 | 30.5 |
| 28 | 2500 | 450 | 5 | 2 | 61.1 | 83.4 | 51.0 |
| 29 | 250 | 390 | 100 | 2 | 94 | 72 | 67.7 |
| 30 | 4000 | 350 | 5 | 2 | 73.3 | 60.5 | 44.3 |
| 31 | 2000 | 350 | 5 | 2 | 54.3 | 60.0 | 32.6 |
| 32 | 350 | 410 | 100 | 2 | 96 | 53 | 50.9 |
| 33 | 60 | 350 | 100 | 2 | 89 | 53 | 47.2 |
| 34 | 250 | 390 | 100 | 2 | 94 | 56 | 52.6 |
| 35 | 500 | 430 | 100 | 2 | 98 | 50 | 49.0 |
| 36 | 250 | 390 | 100 | 2 | 98 | 32 | 31.4 |
| 37 | 800 | 390 | 100 | 2 | 57 | 67 | 38.2 |

We claim:

1. A process for producing an N-substituted aziridine compound represented by general formula (II)

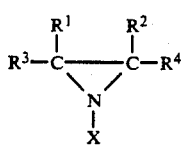

(II)

wherein $R^1$, $R^2$, $R^3$ and $R^4$ are each independently a member selected from the group consisting of a hydrogen atom and alkyl groups of 1–4 carbon atoms, and X is a member selected from the group consisting of hydroxyalkyl groups of 1–4 carbon atoms and aminoalkyl groups of 1–4 carbon atoms, which process is characterized by subjecting to a gas phase intramolecular dehydration reaction in the presence of a catalyst an N-substituted alkanolamine represented by general formula I

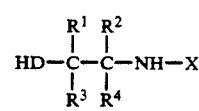

(I)

wherein $R^1$, $R^2$, $R^3$, $R^4$ and X each have the same definition as in general formula (II), said reaction being conducted under conditions of reaction pressure of from about 5 to 50 mmHg (absolute pressure), reaction temperature in the range of from about 300° to 450° C. and space velocity in the range of from about 50 to 500 $hr^{-1}$ (STP).

2. The process according to claim 1, wherein the catalyst is a composition represented by the general formula $X_aP_bM_cO_d$ wherein X represents at least one element selected from the elements of group IIIA of periodic table, the elements of group IVA, the elements of group VA, the transition metal elements of groups I and VIII, the lanthanide elements and the actinide elements, P represents phosphorous, M represents at least one element selected from the alkali metal elements and the alkaline earth metal elements, O represents oxygen, the suffixes a, b, c and d represent the ratios of the atom numbers of the individual elements, when $a=1$, b is in the range of 0.01 to 6 and c is in the range of 0.01 to 3, and d is a value determined by the values of a, b and c and further by the state of bonding of the constituent elements.

3. The process according to claim 1, wherein the catalyst is a composition represented by the general formula $Si_aM_bY_cO_d$ wherein Si represents silicon, M represents at least one element selected from the alkali metal elements and the alkaline earth metal elements, Y represents at least one element selected from boron, aluminum, titanium, zirconium, tin, zinc and cerium, O represents oxygen, the suffixes a, b, c and d represent the ratios of the atom numbers of the individual elements, when $a=1$, b is in the range of 0.005 to 1 and c is in the range of 0.005 to 1, and d is a value determined by the values of a, b and c and further by the state of bonding of the constituent elements.

* * * * *